(12) United States Patent
Huttel et al.

(10) Patent No.: US 6,495,842 B1
(45) Date of Patent: Dec. 17, 2002

(54) IMPLANTATION OF THE RADIOACTIVE $^{32}$P ATOMS

(75) Inventors: Erhard Huttel, Eggenstein-Leopoldshafen; Johann Kaltenbaek, Stutensee; Klaus Schlosser, Eggenstein-Leopoldshafen; Ludwig Friedrich, deceased, late of Karlsruhe, all of (DE), by Ingeborg Friedrich, executrix

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 272 days.

(21) Appl. No.: 09/597,117

(22) Filed: Jun. 20, 2000

Related U.S. Application Data

(63) Continuation-in-part of application No. PCT/EP98/08379, filed on Dec. 21, 1998.

(30) Foreign Application Priority Data

Dec. 24, 1998 (DE) .......................... 197 57 852

(51) Int. Cl.$^7$ .................... H01J 37/317; H01J 37/08
(52) U.S. Cl. ............... 250/492.3; 250/423 R; 315/111.21; 315/111.41; 315/111.51; 315/111.81
(58) Field of Search ................. 250/492.21, 492.3, 250/423 R; 315/111.21, 111.41, 111.51, 111.81

(56) References Cited

U.S. PATENT DOCUMENTS

| | | | |
|---|---|---|---|
| 3,778,656 A | 12/1973 | Fremiot et al. ............... | 313/63 |
| 4,778,561 A | 10/1988 | Ghanbari .................... | 156/643 |
| 4,780,642 A | 10/1988 | Jacquot .................... | 313/359.1 |
| 4,992,665 A | 2/1991 | Möhl ..................... | 250/423 R |
| 5,607,442 A | 3/1997 | Fischell et al. ............. | 606/191 |
| 5,898,178 A * | 4/1999 | Bunker .................... | 250/423 R |

* cited by examiner

*Primary Examiner*—Jack Berman
(74) *Attorney, Agent, or Firm*—Klaus J. Bach

(57) ABSTRACT

In an apparatus for the doping of vessel supports (stents) with radioactive and non-radioactive atoms comprising an electron-cyclotron-ion-source (ECRIS) with an arrangement for extracting an ion beam from the ECRIS, a magnetic separation device for the splitting of the ion beam arranged in a downstream area of the extracted ion beam and an irradiation chamber in which the vessel supports are exposed to the selected partial ion beam, the ECRIS includes a microwave-permeable plasma chamber with a magnetic, six-pole arrangement, an electrically conductive tube portion disposed within the plasma chamber co-axially with the six-pole arrangement and having an in-coupling opening and also being axially movable for an adjustment of an optimal in-coupling and a co-axial cable extends through the in-coupling opening and has an outer sleeve which is in electrical contact and an inner conductor which is electrically insulated and forms at the inner wall of the tube a flat loop whose end is in contact with the tube wall.

8 Claims, 3 Drawing Sheets

| Mass | Radioactive | Non-radioactive |
|---|---|---|
| 31 | -- | $31P^+$ |
| 32 | $32P^+$ | $(31PH)^+$ |
| 33 | $(32PH)^+$ | $(31PD)^+ (31PH_2)^+$ |
| 34 | $(32PD)^+ (32PH_2)^+$ | $(31PDH)^+$ |
| 35 | $(32PDH)^+ (32PH_3)^+$ | $(31PD_2)^+ (31PDH_2)^+$ |
| 36 | $(32PD_2)^+$ | $(31PD_2H)^+$ |
| 37 | $(32PD_2H)^+$ | $(31PD_3)^+$ |
| 38 | $(32PD_3)^+$ | |

IMPLANTATION OF THE RADIOACTIVE $^{32}$P ATOMS

This is a continuation-in-part application of international application PCT/EP98/08379 filed Dec. 21, 1998 and claiming the priority of German application 197 57 852.7 filed Dec. 24, 1998.

BACKGROUND OF THE INVENTION

The invention resides in an Electron-Cyclotron-Resonance-Ion-Source (ECRIS) and a method for the operation of such an ECRIS and to vessel supports (stents) which have been doped with radioactive and non-radioactive atoms and molecules.

Such vessel supports, called stents in professional terminology, are used in the medicine in the treatment of vessel stenoses. For such treatment, struts are doped with a radioactive element whose half-life depends on the healing period for a surgical injury. Residual stenoses are to be prevented thereby.

Since the half-life is a relatively short period—14 days is a reasonable period—such stents cannot be stored. Rather, these stents must be doped quantitatively and in a reproducible manner with the suitable radioactive element, wherein the radioactivity remaining at the time of insertion into the human body, the transport distance and the transport time from the doping up to the implantation must be taken into consideration for the doping prescription.

There is therefore the question what the optimal irradiation procedure is and with what kind of apparatus such irradiation can be reliably and reproducibly performed.

Such an irradiation apparatus consists of three main components, that is, an ion source with a extraction system, a mass separation device in the form of a dipole magnet and an irradiation chamber. It is known that electron-cyclotron-resonance-ion sources provide a large amount of ion radiation of high quality. Such an ion source is therefore part of the apparatus. A mass separator is a dipole magnet which fans out, in a mass-specific manner, the extracted ion beam, while the beam passes through the mass separator passage. Finally, in the irradiation chamber, the object is subjected to the selected partial beam for doping. The insertion into and removal of the object or objects from, the irradiation chamber occurs by flushing the chamber with argon and then opening the chamber.

ECR ion sources are explained in, among others, the handbook "Ion Sources", published by Bernhard Wolf, 1995, CRC Press Boca Raton, New York, London, Tokyo. It provides an overview with hints to other sources. The basic ECRIS is described in this book among others in sections 9.2 "Working Principle of the Ion Source and Description of the Discharge" on pages 122 to 127. The book "Electron Cyclotron Resonance Ion Sources and ECR Plasmas" by R. Geller, Institute of Physics Publishing, Bristol and Philadelphia, 1996 is more explicit and detailed. In this book, in addition to the chapter 2.4, Antennas and Coupling Structures, the chapter 5 "Simple Mirror ... " and 6, Min-B ECRIS for ... " are very explicit, particularly with respect to the source design.

ECR sources were first used mainly for the generation of highly charged ions for which microwaves of higher frequencies are needed. The use of lower frequencies still provides the advantage of a high ion yield, which is what is important here. Economically the use of lower microwave frequencies has the advantage that, for 2.45 GHz, reasonably priced microwave generators are available and furthermore only comparatively low magnetic fields are necessary. It is however difficult with these low frequencies to couple the microwaves to the plasma if the wavelengths are greater than the dimensions of the plasma chamber.

It is the object of the present invention to provide a reliable ECR ion source which exhibits a good long-term behavior so that one, or at the same time, more stents disposed in the irradiation chamber are subjected to a partial beam of constant quality from an ion beam which has been well fanned out mass-specifically in a reproducible manner for doping of the stents.

SUMMARY OF THE INVENTION

In an apparatus for the doping of vessel supports (stents) with radioactive and non-radioactive atoms comprising an electron-cyclotron-ion-source (ECRIS) with an arrangement for extracting an ion beam from the ECRIS, a magnetic separation device for the splitting of the ion beam arranged in a downstream area of the extracted ion beam and an irradiation chamber in which the vessel supports are exposed to the selected partial ion beam, the ECRIS includes a microwave-permeable plasma chamber with a magnetic, six-pole arrangement, an electrically conductive tube portion disposed within the plasma chamber co-axially with the six-pole arrangement and having an in-coupling opening and also being axially movable for an adjustment of an optimal in-coupling and a co-axial cable extends through the in-coupling opening and has an outer sleeve which is in electrical contact and an inner conductor which is electrically insulated and forms at the inner wall of the tube a flat loop whose end is in contact with the tube wall.

The six-pole magnet arrangement radially surrounding the plasma chamber is disposed in a dielectric tube and consequently insulates each of the solenoids which are disposed in the two end areas of the plasma chamber co-axially around the axis. This substantially improves the high voltage safety. Preferably, there is a foil in the tube, which has the advantage that no electrostatic field peaks can occur on the inner surface of the dielectric tube as they would occur with the sharp-edged structure of the six-pole arrangement without the use of the foil. Since the foil has no electrically conductive connection with the six-pole arrangement, it is charged at the edges by corona discharge so that the field strengths resulting in this discharge are partially compensated for whereby the corona discharge is again reduced.

The di-electric tube preferably consists of plexiglas, which is transparent and therefore facilitates a very good recognition of changes or damages as they may be caused by electrical stresses or thermal stresses.

The plasma chamber is preferably a (double-wall) Pyrex tube. In this way, the microwave energy can be coupled radially into the tube from all sides. The plexiglas has only a small recombination coefficient, which provides for a neutral gas share with a high hydrogen atom content. Hydrogen is chemically aggressive only in the atomic state (hydrogen nascendi) and reacts with phosphorus condensed on the wall to form gaseous phosphor hydrogen.

It is reasonable to operate the source continuously. A timed operation—which would basically be possible—would be disadvantageous since, during the period in which the ion source is switched off, losses of radioactive phosphor hydrogen would still occur.

According to the basic process for operating the ECRIS, basically, the process should be maintained continuous. Masking out of a partial beam from the total beam depending on the gas and additional gas filling as well as the adjustment of the electrical operating parameters for the ECRIS and the separation magnet and of the exposure position of the stents should be, and is, possible, as will be explained later on the basis of FIG. 3.

An important electrical parameter is the adjustability of the high voltage of the ECRIS for the extraction.

The vessel support structure, that is the stent may be subjected to a partial beam selected from the ECRIS operated by the process.

The additional implantation of non-radioactive atoms changes the stents in an advantageous manner by preventing premature flushing during positioning of the stents and in their final positions.

The ECR ion source provides an ion beam of sufficient energy so that its useful part penetrates sufficiently deep into the stents. The energy is for example 60 keV. The microwave guiding requires no space beyond the space provided for the six pole arrangement. Another advantage of the apparatus is that additional ions for example suitable molecule ions are admixed to the beam provided by the separation magnet. They are implanted into the objects together with the radioactive and non-radioactive atoms, whereby the quality of the objects regarding corrosion and erosion of radioactivity is improved.

The invention will be described below in greater detail on the basis of the accompanying drawings. The drawings include FIGS. 1 to 3 and a table.

DESCRIPTION OF PREFERRED EMBODIMENTS

The ion source operates with small amounts of substances of radioactive phosphorus. About 5 mg of natural phosphorus ($^{31}P$) is enriched with $10^{-5}$ radioactive phosphorus ($^{32}P$) An as high as possible percentage of the radioactive phosphorus atoms, which are introduced into the ion source should be transferred into the high-energy beam of atom and molecule ions which is separated out by the separation magnet 2. The ion source 1 provides an ion beam from which a useable part is made accessable by the separation magnet 2. The useable part of the ion beam includes a sufficiently large share of radioactive phosphorus atoms or phosphorus molecules so that the dosis required for a particular application can be implanted into the stents.

Figure 1:
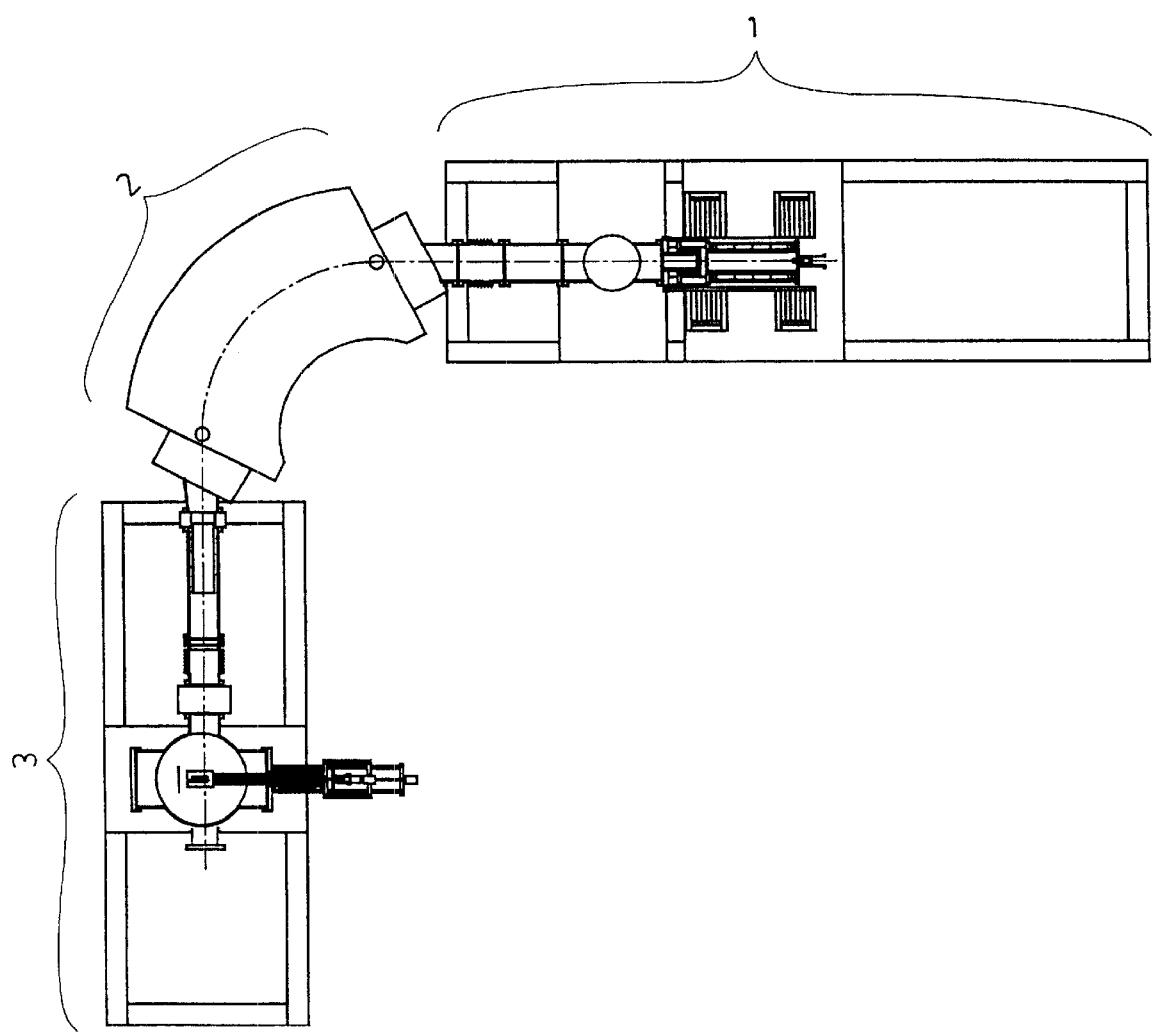
FIG. 1 shows a schematic arrangement of the apparatus.

The apparatus arrangement comprises three components: an electron-cyclotron-resonance-ion-source 1, a separation magnet 2 and an irradiation chamber (3 FIG. 1). The ion beam is generated with the ECR-ion source 1 and is extracted therefrom in the direction toward the separation magnet 2, in which it is fanned out and prepared in a mass-specific manner. The devices exposed in the irradiation chamber 3, that is, the vessel support devices or stents are so arranged that the useable part of the ion beam, which consists of high energy radioactive phosphorus ions or non-radioactive phosphorus molecule ions impinges on the support devices and is implanted into the structural material of the support devices as radioactive or non-radioactive phosphorus atoms.

Figure 2:
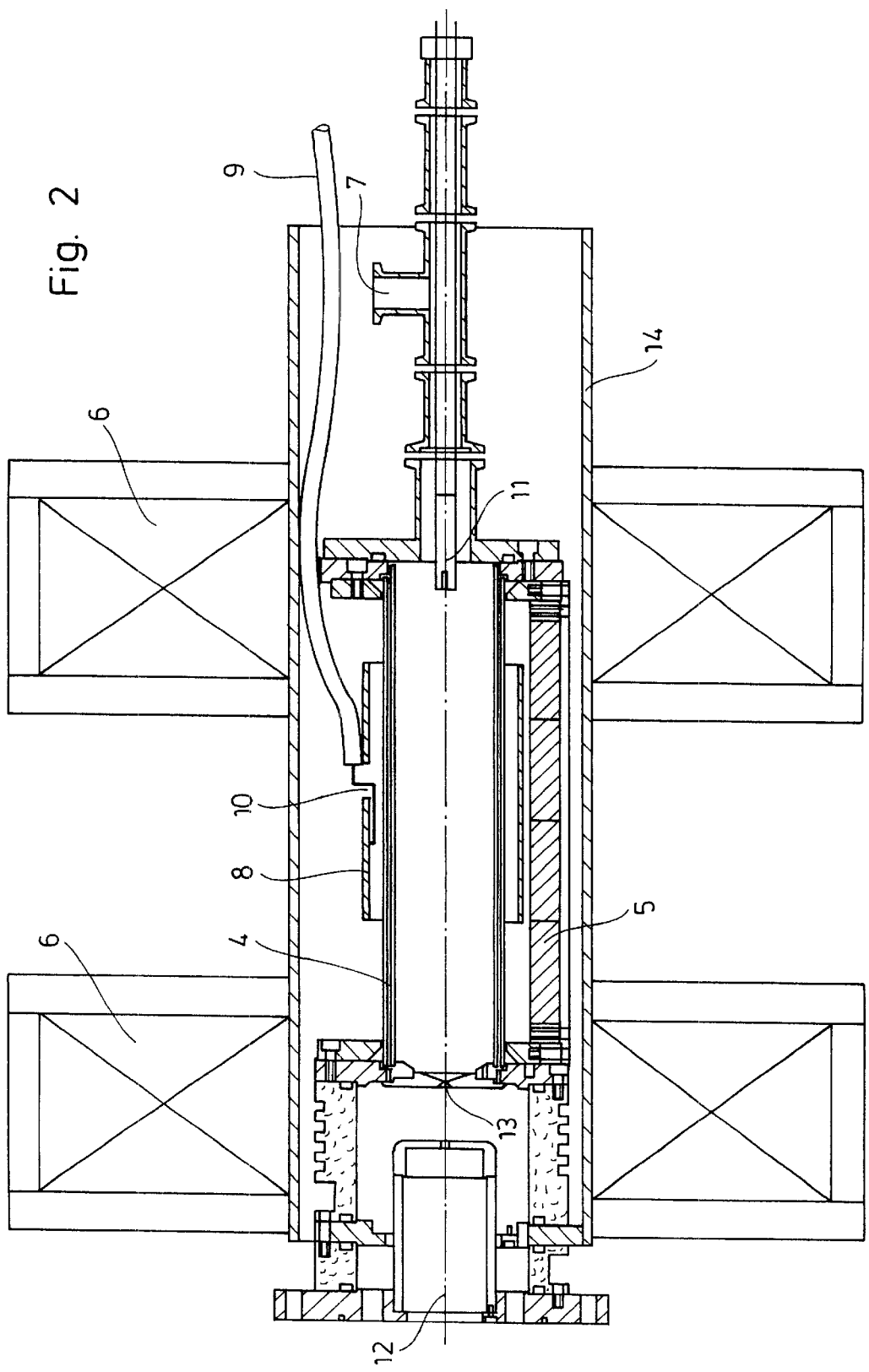
FIG. 2 shows a schematic arrangement of the ECR ion source.

FIG. 2 shows the ECR ion source in an axial cross-sectional view. The cylindrical plasma chamber 4, whose walls are transparent for microwaves and consist of a material which has an as small as possible recombination coefficient with respect to the formation of molecules from atoms of the added gas, is disposed concentrically within the six-pole magnet 5. Around both ends of the six-pole magnet and the ends of plasma chamber, the magnetic mirror coils 6 are disposed. A suitable gas such as hydrogen or deuterium is supplied to the plasma chamber 4 by way of a gas inlet 7. The gas is ionized by the microwave coupled into the chamber 4. With the magnetic six-pole field and the axial magnetic mirror field, only few of the electrons formed during the ionization will reach the wall of the plasma chamber 4. As a result, a large electron density develops in the plasma chamber and the electrons, driven by the microwaves because of the electron-cyclotron resonance, are subjected in the plasma chamber 4 to an oscillating motion. As a result, the gas in the plasma chamber 4 becomes ionized to a high degree.

For the in-coupling of the microwave, a thin-walled tube piece 8 is disposed concentrically between the plasma chamber 4 and the six-pole permanent magnet 5 in such a way that it is axially slideable back and forth. The microwave is supplied to the tube piece 8 by way of a thin coaxial cable 9. To this end, the outside surface of the coaxial cable 9 is disposed in contact with the tube piece 8 at the in-coupling opening 10 and ends there. The inner conductor extends through this opening 10 inwardly. The insulated inner conductor forms a loop extending parallel to the center axis 12 and is in contact with the inner wall of the tube piece 8. The microwave is coupled into the tube piece 8 by this loop. This engagement provides for the following advantages:

i. With the axial slideability of the tube piece 8, the difficulty encountered with the coupling of the microwaves to the plasma, which is caused by the fact that the wave length is greater than the chamber dimensions so that the microwave energy cannot sufficiently spread out in the plasma chamber, is circumvented. It is then possible to move the tube piece 8 to a location wherein the maximum field strength of the microwaves is in the range of the magnetic resonance field strength.

ii. Only a relatively small amount of microwave energy is needed so that the microwave energy can be supplied by a thin coaxial cable parallel to the axis of the ion source 1 between the six-poles 5. With this supply arrangement for the microwaves, which does not negatively affect the ion source arrangement, the complete ECR ion source, with the exception of the mirror coils 6, can be kept electrically insulated by a dielectric tube, here a plexiglass tube and can be operated therefore without problems at 60 kV or higher. Consequently, the energy impression of the ion beam is adjustable within wide limits.

The radioactive phosphorus is impressed into the support member 11, which is placed into the ion source. By interaction with the plasma, which is operated with hydrogen or deuterium gas, the phosphorus is transferred thereto and is re-deposited almost instantly on the wall of the plasma chamber 4.

It is advantageous to use $H_2$ or $D_2$ for the generation of the plasma if the inner wall of the plasma chamber consists of Pyrex®, which has a low recombination coefficient with regard to the formation of molecules from hydrogen- or deuterium atoms. Then a high density of hydrogen or respectively, deuterium atoms and ions in the plasma chamber is obtained which react chemically with phosphorus deposited on the inner wall of the plasma chamber. As a result, gaseous phosphorushydrogen compounds are formed which fall back into the reaction chamber, whereby phosphorus is returned to the plasma.

The ECR ion source is operated at a very low neutral gas pressure and a high ion content. For the ion extraction, there is only a small opening 13 provided in the plasma chamber 4. The ECR ion source therefore loses only few neutral atoms and molecules. The phosphorus leaves the ion source mainly either as atom ions or as molecule ions of the various phosphorus hydrogen molecules in the extracted high energy ion beam, in this case for example 60 keV. The use of the chemical process is advantageous for fulfilling the requirements to use only small amounts of radioactive substances and that the ion beam leaves the spectrum magnets rich in energy and sufficiently enriched with radioactive ions.

Figures 3, 4:
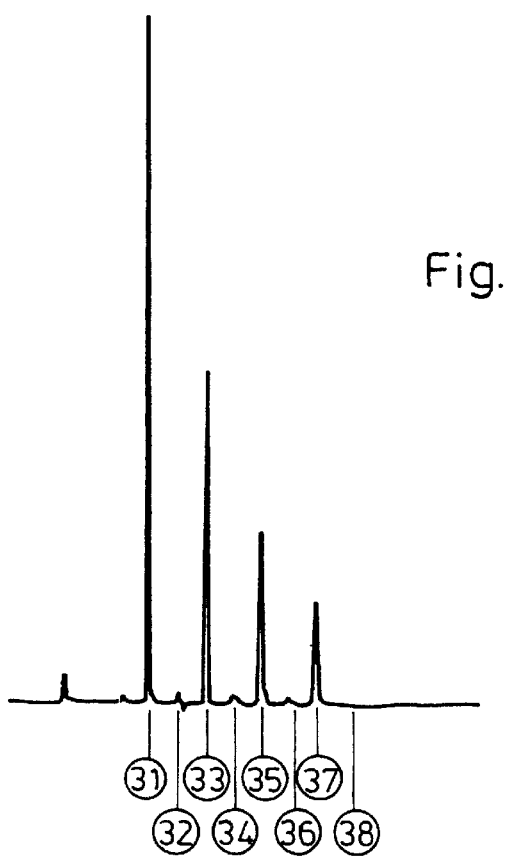
FIGS. 3 and 4 show the mass spectrum of the ECR-ion source for radioactive phosphorus and, in the table, the possible mass parts.

FIG. 3 shows a section of the mass spectrum generated if the ECR ion source is operated with radioactive phosphorus. The operating parameters are as follows: The ion source is operated with $D_2$. 5 mg $^{32}P$ are added, of which a part of about $10^{-5}$ is enriched with radioactive $^{32}P$. It is known that phosphorus can bind up to three H- or respectively D atoms. Basically, in the plasma, also phosphorus molecule ions can be formed which include only one or two hydrogen or respectively, deuterium atoms. The masses correspond to the ions of the pure atoms $^{31}P$ and $^{32}P$ and or a multitude of combinations of phosphorus hydrogen- or, respectively, phosphorus deuterium ions. Mass numbers of 31, normal phosphorus, up to 38, fully deuteriumized radioactive phosphin may occur. The prototype ion source generally supplies 30 $\mu A$ non-radioactive $^{31}P^+$ ions.

From the table, the following conclusions can be drawn:

If the content of normal hydrogen in the plasma is kept sufficiently low and the separation magnet is adjusted to the mass 32, a beam can always be generated which contains sufficient parts of radioactive phosphorus for doping the stents needed in the medicine with radioactive phosphorus $^{32}P$.

If the source is operated with pure deuterium ($D_2$) and hydrogen ($H_2$) is admixed in a predetermined manner, radioactive phosphorus and non-radioactive phosphorus is implanted with the same beam. In this way, the quality of the irradiated article, that is, the stent is improved with respect to corrosion and flushing out of the radioactivity.

What is claimed is:

1. An apparatus for the doping of vessel support structures with radioactive and non-radioactive atoms, comprising an Electron-Cyclotron-Resonance-Ion-Source (ECRIS) with an ion extraction arrangement for extracting an ion beam from said ECRIS, a magnetic separation device for the mass-specific splitting of the ion beam arranged in a downstream area of the ion beam extracted and an irradiation chamber in which the vessel supports are exposed to the selected partial ion beam, said apparatus including a microwave permeable cylindrical plasma chamber with a six-pole magnet arrangement equally distributed over the circumference of said cylindrical plasma chamber, a thin-walle electrically conductive tube portion disposed co-axially between the cylindrical plasma chamber and said six-pole magnet arrangement surrounding said cylindrical plasma chamber, said tube portion having an in-coupling opening in its wall and being axially movable on said cylindrical plasma chamber for an adjustment of the optimal microwave in-coupling, and a co-axial cable having an outer sleeve in electrical contact with said tube portion and an inner conductor extending through said in-coupling opening in an insulated fashion and forming at the inner wall of said tube portion a flat loop having an end in contact with the inner wall of said tube portion.

2. An apparatus according to claim 1, wherein said coaxial cable for supplying the microwaves extends parallel to the axis of the plasma chamber between two poles of the six-pole magnet arrangement.

3. An apparatus according to claim 2, the plasma chamber of said ECRIS and the tube portion with the co-axial cable are surrounded by a dielectric tube in order to electrically isolate the respective co-axially arranged solenoid (6) at the two end areas of the plasma chamber for the generation of the magnetic mirror field for axial enclosure.

4. An apparatus according to claim 3, wherein said dielectric tube is covered by an electrically conductive foil which is spaced therefrom by dielectric strips and is nowhere in electrical contact with the six pole magnet.

5. An apparatus according to claim 4, wherein said dielectric tube consists of plexiglass.

6. An arrangment according to claim 5, wherein said plasma chamber includes a material, or its inner wall is coated by a material which has the smallest possible recombination coefficient, such as Pyrex, with respect to the formation of molecules from the atoms of the gas supplied by way of the inlet.

7. A method of operating an electron-cyclotron resonance source, ECRIS, having an extraction opening forming a magnetic bottle in an apparatus for the doping of vessel support structures (struts) with radioactive and non-radioactive atoms, which apparatus includes a vacuum chamber having a wall of a material with a low recombination coefficient with respect to molecule formation from hydrogen or deuterium and an ion source, said method comprising the steps of:

generating in said vacuum chamber a plasma from hydrogen ($H_2$) and for deuterium ($D_2$), operating the ion source at low gas pressure ($H_2$ and $D_2$) and with high ion content in the area of the effective magnetic bottle of said ECRIS supplying microwave energy through a microwave supply duct to an axially movable metallic tube section which extends concentrically around the vacuum chamber and coupling the microwave energy necessary for the plasma generation into said vacuum chamber by way of said concentric metallic, tube section moving the tube section axially until the maximum field strength of the in-coupled microwave is in the range of the magnetic resonance field strength, exposing a body of phosphorus fitted into a holder of the ion source for interaction with the plasma on the axis of a magnetic mirror field in the area of the neck of said magnetic bottle which is disposed opposite the extraction opening of said ECRIS, whereby phosphorus removed from said body of phosphorus is condensed on the inner wall of the vacuum chamber where the phosphorus reacts chemically with the hydrogen or deuterium to from gaseous phosphorus hydrogen and drops back into the vacuum chamber for the generation of atom ions from the available phosphorus isotopes or the generation of molecule ions of the various phosphorus hydrogens, and withdrawing the atom and molecule ions from the axial area of the vacuum chamber as a continuous ion stream.

8. Method according to claim 7, wherein energy is impressed on the ion beam to be extracted by way of the adjustable high voltage at the rest of the ECRIS which is electrically uncoupled from the two mirror coils by way of a dielectric tube.

\* \* \* \* \*